United States Patent [19]

Briefer et al.

[11] Patent Number: 5,604,315
[45] Date of Patent: Feb. 18, 1997

[54] APPARATUS USING A FEEDBACK NETWORK TO MEASURE FLUID PRESSURES

[75] Inventors: Dennis K. Briefer, Marlborough; Anthony T. Batista, Stow, both of Mass.

[73] Assignee: Setra Systems, Inc., Acton, Mass.

[21] Appl. No.: 371,851

[22] Filed: Jan. 12, 1995

[51] Int. Cl.$^6$ ................................ G01L 9/00; G01F 1/34
[52] U.S. Cl. .................................... 73/861.49; 73/718
[58] Field of Search ........................... 73/861.49, 861.44, 73/861.47, 718, 724, 49.2, 438, 299

[56] References Cited

U.S. PATENT DOCUMENTS

| | | | |
|---|---|---|---|
| 4,358,814 | 11/1982 | Lee et al. | 73/724 |
| 4,434,664 | 3/1984 | Antonazzi | 73/718 |
| 4,457,179 | 7/1984 | Antonazzi et al. | 73/718 |
| 4,561,307 | 12/1985 | Smith | 73/438 |
| 4,765,945 | 8/1988 | Walleser | 73/299 |

Primary Examiner—Richard Chilcot
Assistant Examiner—Harshad Patel
Attorney, Agent, or Firm—Lappin & Kusmer

[57] ABSTRACT

An apparatus is disclosed for measuring the pressure of a liquid column enclosed within a pressurized tank or cell, and for deriving the height and/or density of the liquid column based on the measured pressure. The apparatus includes a first pressure sensor for differentially measuring the pressure within the cell relative to a reference pressure at a first height, and further includes a second pressure sensor for differentially measuring the pressure within the cell relative to a reference pressure at a second height. A feedback network is operative to match the reference pressure to the pressure within the cell at one of the first and second heights. The feedback network ensures that the sensor detecting the one region is maintained at a zero or null differential pressure condition, enabling the use of a small dynamic range sensor.

16 Claims, 5 Drawing Sheets

APPARATUS USING A FEEDBACK NETWORK TO MEASURE FLUID PRESSURES

FIELD OF THE INVENTION

The present invention relates to level sensing apparatus and, more particularly, to a configuration employing differential pressure sensors for determining fluid levels within closed pressurized systems.

BACKGROUND OF THE INVENTION

Transducers are widely used in measurement and control systems for converting a physical quantity into a corresponding signal suitable for processing. A pressure transducer is a sensor which may respond to an applied fluid pressure and produce a signal (e.g., electrical, mechanical, or pneumatic) representative of the pressure. Typically, a pressure transducer may utilize a pressure-sensitive element where that element includes a portion having a position that varies with applied pressure. That position is transformed into an electrical signal representative thereof.

A particular class of pressure transducers employs a peripherally supported diaphragm as the pressure sensitive element, and operates in response to an applied pressure to translate a physical displacement of the diaphragm into an electrical signal. One prior art form of diaphragm transducers utilizes a capacitive-sensing arrangement for accomplishing the displacement-to-electrical signal conversion. FIG. 1 shows a prior art capacitive pressure sensor 10 including a relatively thin, edge-supported, electrically conductive diaphragm element 20 disposed across a concave base member 14 that houses a first distinct region 26 below diaphragm 20 and a second distinct region 33 above diaphragm 20. The two regions may be separately pressurized by couplings attached to pressure ports 12 and 16 to establish a pressure differential across diaphragm 20. The central portion of diaphragm 20 is movable in the direction of axis 14a in response to that pressure differential. Sensor 10 further includes an electrode element 32 within region 26 that serves as an electrically conductive element that is opposite and nominally separated by a distance d from a corresponding region of diaphragm 20. Accordingly, diaphragm 20 and electrode 32 effectively establish a "parallel" plate capacitor having a characteristic capacitance that varies inversely with d, which value is related to the pressure differential across diaphragm 20. Transducers of this configuration are described in U.S. Pat. No. 4,358,814 assigned to Setra Systems, Inc., the assignee of the present invention. Sensors of this type thus produce an electrical characteristic (i.e., capacitance between electrode 32 and the diaphragm) that is representative of the distance d, which in turn is representative of the pressure differential across the diaphragm; that differential may be established by either gas or liquids in two respective regions on either side of the diaphragm.

Diaphragm-based pressure transducers are useful in industrial applications requiring pressure measurements of a liquid column enclosed within a pressurized cell. For example, the height of the liquid column may be derived from the measured column pressure. However, conventional level-measuring apparatus are currently limited in their ability to precisely measure fluid levels in such cells, creating particular difficulties for biomedical applications where significant bioactive processing occurs in these cells. The conventional apparatus described below are noteworthy for such problems as nonsanitary couplings to the interior of the cell and requirements for costly high dynamic range sensors.

In a typical closed, pressurized cell or tank system where it is desired to measure the level of a liquid in the tank, there are two component pressures of interest: one corresponding to the "total pressure," that is, the pressure at the bottom of the tank due to the weight of the liquid as burdened by the blanket pressure (i.e., the pressure in the region above the liquid), and the other corresponding to the blanket pressure. One conventional level measurement system is shown in FIG. 2A for a pressurized cell or tank 19 enclosing a liquid column 21 and an overlying blanket region 20. The illustrated system employs a combination of pressure sensors (exemplified by the illustrated diaphragm pressure transducers and associated sensor networks) that independently measure total pressure and blanket pressure. The difference between the independent measurements is reported as the pressure of the liquid column. As shown, an upper pressure transducer 22, positioned at or near the top of tank 19, includes a diaphragm 23 flush to the cell wall for detecting the pressure of blanket region 20. The resultant pressure is converted to an electrical signal by associated sensor network 24, producing an output on line 25. A similar pressure transducer 26, positioned at or near the bottom of tank 19, includes a diaphragm 27 flush to the cell wall for detecting the total pressure of the cell, namely the pressure of liquid column 21 plus the pressure of blanket region 20. This pressure differential is convened to an electrical signal by associated sensor network 28, producing an output on line 29. The signals on lines 25 and 29 may be differenced to produce a signal representative of the level of liquid column 21.

The gauge-type pressure measurements of FIG. 2A require that transducer 22 and associated network 24 have a full scale range at least as high as the maximum blanket pressure, and that the transducer 26 and associated network 28 have a full scale range at least as high as the total cell pressure. This requirement therefore demands that both transducers have a large dynamic range since the pressure in the blanket region may vary widely as the liquid level moves from the top of the tank to the bottom. For example, the liquid column may produce a pressure of only 4±0.5 psi over the range of levels, while the blanket pressure may vary in the range of 20–50 psi, an appreciable contribution to the total cell pressure. Since the overall accuracy of the sensor's measurement capability is a function of the accuracy of the individual pressure sensors, which in turn is specified as a percentage of full range, a high accuracy system may only be constructed using costly, large dynamic range sensors.

FIG. 2B illustrates another conventional level sensing system similarly having two flush diaphragm sensing elements, but employing liquid-filled capillary tubing to couple the diaphragm displacements to a single differential diaphragm transducer 31 and an associated sensor network 32. The system comprises an upper isolation assembly 22 including a diaphragm 23 flush to an upper portion of the cell wall for detecting the pressure of blanket region 20, and further comprises a lower isolation assembly transducer 26 including a diaphragm 27 flush to a lower portion of the cell wall for detecting the total pressure of the cell. In this configuration, the pressure detected by each of diaphragms 23 and 27 is hydraulically transmitted to the diaphragm 31A of transducer 31 using a respective one of silicone oil-filled capillary tubes 30A and 30B. This connectivity to the remotely-positioned transducer 31 introduces the risk of media contamination due to leakage of silicone oil from transducer 31 or the connecting capillary tubes or isolation assemblies 22 and 26. Additionally, any physical displacement or thermally-induced unbalanced expansion of the liquid-filled tubes will cause erroneous pressure signals to be presented to the diaphragm 31A, thereby leading to faulty or inaccurate readings at the output 32A.

FIG. 2C shows an additional prior art level measuring system utilizing a single differential diaphragm transducer 31 that senses the blanket pressure, as coupled by pneumatic line 34, with respect to the fluid pressure created by the displacement of a flush diaphragm 27, as coupled by silicone oil-filled capillary tube 30B, for detecting the total pressure of the cell. In this configuration, the pressure of blanket region 20 is communicated to sensor 31 via line 34 through a non-flush, non-sanitary reference pressure port of sensor 31. The capillary attachment is a drawback to this configuration because it exposes the media within the cell to additional environments (e.g., tubing) external to the cell. This configuration is thus precluded from any application requiring absolute clean-in-place (CIP) or steam-in-place (SIP) sanitation processing.

FIG. 2D is a yet further prior art system that is similar to the FIG. 2C apparatus, but replaces the nonflush/nonsanitary reference port and capillary tube 34 with a pneumatic pressure repeater 36 coupled to pressure transducer 22 having flush diaphragm 23. The pressure repeater 36 provides a secondary pneumatic signal to the blanket input port of differential sensor 31. This configuration avoids problems created by the configuration of FIG. 2C due to the non-flush, non-sanitary port. However, although the pneumatic pressure repeater 36 is a relatively reliable instrument, there is no mechanism in this configuration for eliminating or compensating for any errors arising from the signal to pneumatic conversion; rather, these conversion errors combine additively with the total system inaccuracy. Any such error elimination or compensation would require a sophisticated, and correspondingly costly, pressure repeater having a sufficient degree of accuracy to avoid or overcome the additive effect of any conversion errors, thus adding an undesirable level of complexity to this configuration.

Accordingly, it is an object of the present invention to provide an improved liquid level measuring system for a pressurized cell.

Another object is to reduce the dynamic range required of the pressure sensors in such systems and to eliminate the use of capillary tubing in constructing a fully sanitary measuring system.

It is a further object of the present invention to reduce measurement errors that may be introduced by any of the elements or instrumentalities used in a liquid level measuring apparatus.

SUMMARY OF THE INVENTION

The present invention is an apparatus for measuring characteristics of liquid column in a pressurized cell. The apparatus comprises a first pressure sensor for measuring the pressure in the cell at a first height H1 in relation to a reference pressure, and a second pressure sensor for measuring the pressure in the cell at a second height H2 (lower than the first height) in relation to a reference pressure. Each of the first and second pressure sensors is a differential pressure sensor, and preferably a pressure transducer with a diaphragm having one side coupled flush to a region interior to said cell, and an opposite side coupled via a reference port to an applied reference pressure.

A feedback network is used to equalize the reference pressure to the pressure in the cell at one of the first and second heights. In one form the feedback network is responsive to the differential measurement from the first pressure sensor to generate the reference pressure, which is in turn applied to the reference port of both pressure sensors, so that the diaphragm of that first pressure sensor is maintained at a null position, as described below.

Alternatively, the feedback may be similarly configured but responsive to the second pressure sensor. In yet another form, the reference pressure may be generated by a third pressure sensor which senses pressure at or near the top of the cell.

Preferably, the feedback network comprises a proportional-plus-integral-plus-derivative controller that is responsive to the differential measurement from a pressure sensor to generate a compensation signal indicative of any deviation of the differential measurement from a zero differential pressure value. A pneumatic signal generator is responsive to the compensation signal to generate a pneumatic reference signal that is representative of the compensation signal, and applies the pneumatic signal as the reference pressure to the reference ports of each of the first and second pressure sensors. The feedback network may take other forms.

In these configurations, a sensor transducer and feedback network cooperatively form a pressure balance feedback loop, which dynamically maintains the diaphragm of the one of the first or second sensor transducers in a null position. The null position of the that sensor is characterized by a zero differential pressure condition whereby the applied reference pressure is in equilibrium with the pressure in the cell at its location in the cell. Since substantially no movement of the diaphragm is required due to the nulling of its position in the steady-state loop operation, this transducer may be a low cost, small dynamic range device. In cases where the first sensor transducer is positioned above the liquid column, and that transducer is nulled, since the blanket pressure is in effect applied to both inputs of the second sensor, its diaphragm primarily moves only in response to changes in the column pressure, which is relatively small. Accordingly, the second sensor may also be an inexpensive, small dynamic range device.

A differencing network generates an output signal $P_c$ representative of the difference in the pressure measurement from the second sensor transducer and the first sensor transducer. Where the first sensor transducer is above the liquid level, and the second sensor transducer is at the bottom of the cell, that output signal $P_c$ is equal to $\rho g L$, where $\rho$ is the density of the liquid, g is the gravitational constant, and h is the height of the liquid column. Thus the level (relative to H1) is $$L = P_c / \rho g.$$

Where the first and second sensor transducers are both below the surface the liquid, but separated by distance h in the vertical direction, the output signal $P_c$ may be used to determine the density of the liquid in accordance with $$\rho = P_c / gh.$$

BRIEF DESCRIPTION OF THE DRAWINGS

For a fuller understanding of the nature and the objects of the invention, reference should be made to the following detailed description and the accompanying drawings in which like reference numerals refer to like elements and in which.

DETAILED DESCRIPTION OF THE PREFERRED EMBODIMENTS

In accordance with the present invention, apparati and methods are shown and described for determining the density of a segment of a liquid column in a cell determining the level of a liquid column enclosed within a sealed and pressurized cell or tank. As discussed below in greater detail, in one form, the pressure of the liquid column, as burdened by the blanket pressure, is differentially measured relative to a reference pressure with a diaphragm transducer. The pressure of the blanket region overlying the liquid is differentially measured relative to the same reference pressure with a diaphragm transducer. A closed-loop feedback network automatically adjusts the reference pressure so that it dynamically tracks the pressure of the blanket region and applies that reference pressure for use in the above noted differential pressure measurements, thereby reducing the dynamic range of the differential measurements in comparison to the range required in gauge-type and other open-loop sensor devices. The difference in pressures measured by the two transducers may be used to determine the height of the column of liquid above the lower transducer. In another form, where both sensors are below the liquid level, a similar arrangement is used to determine the density of the portion of the liquid column between the two sensors.

Figure 1:
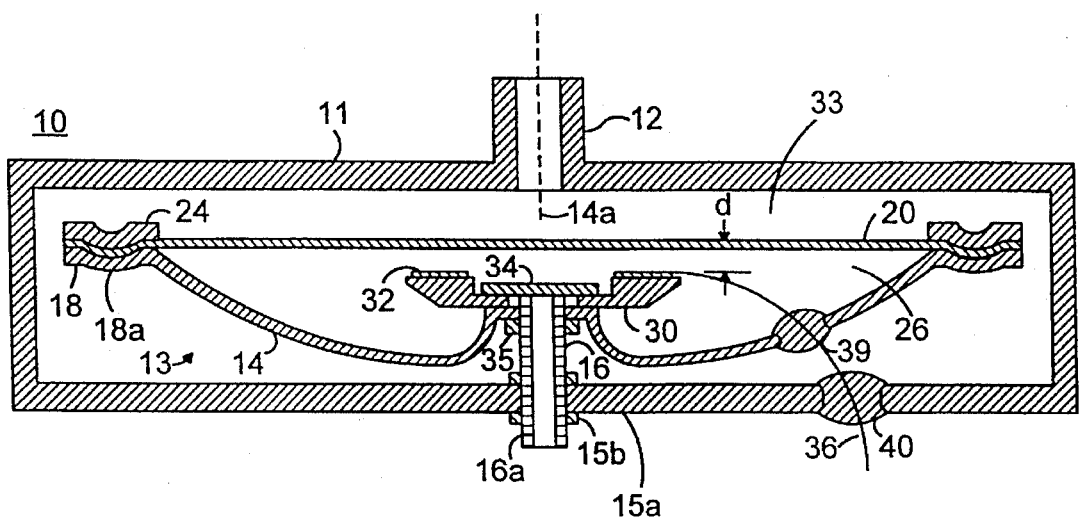
FIG. 1 shows a prior art diaphragm pressure transducer.
Figure 2A:
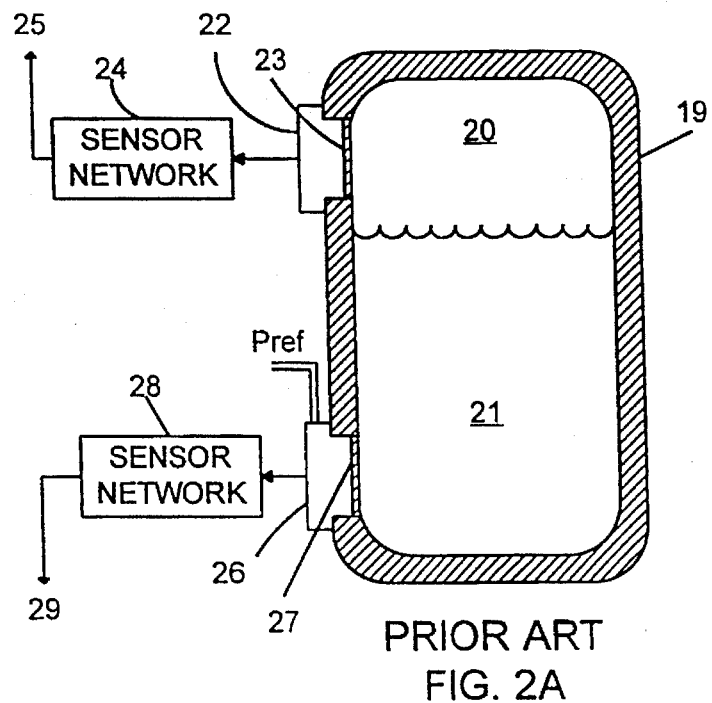
FIGS. 2A–D show a series of prior art configurations for measuring fluid pressures in a pressurized tank.
Figure 2B:
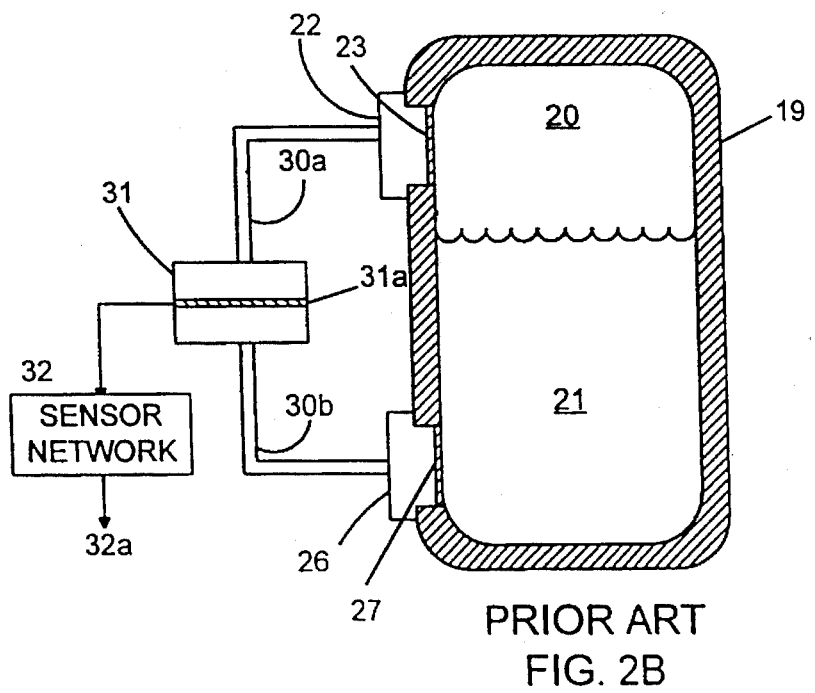
Figure 2C:
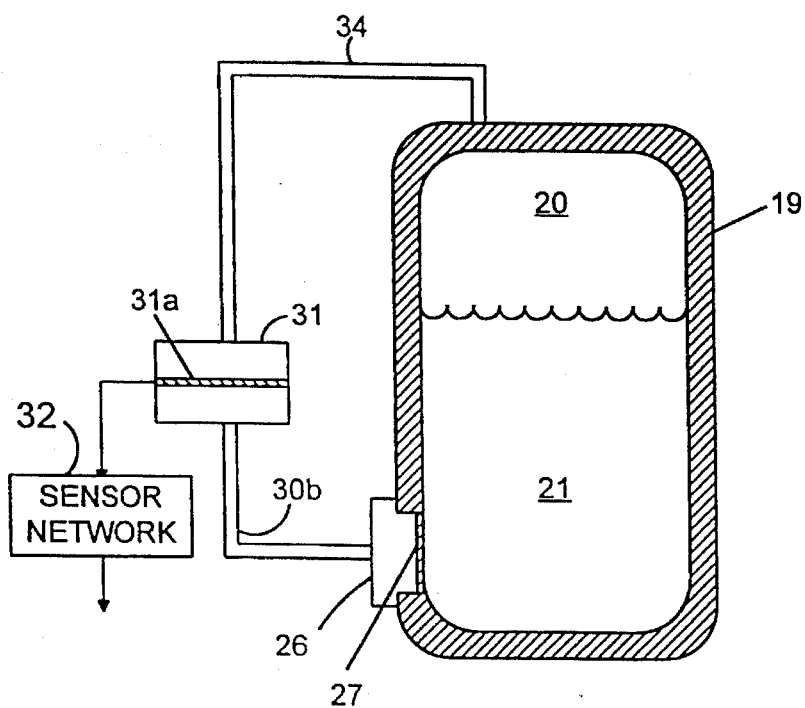
Figure 2D:
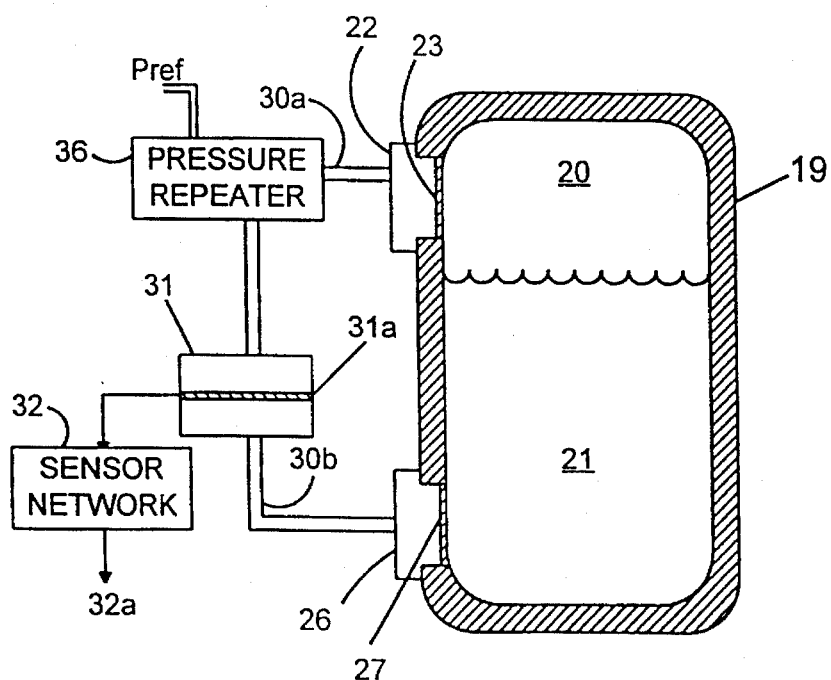
Figure 3B:
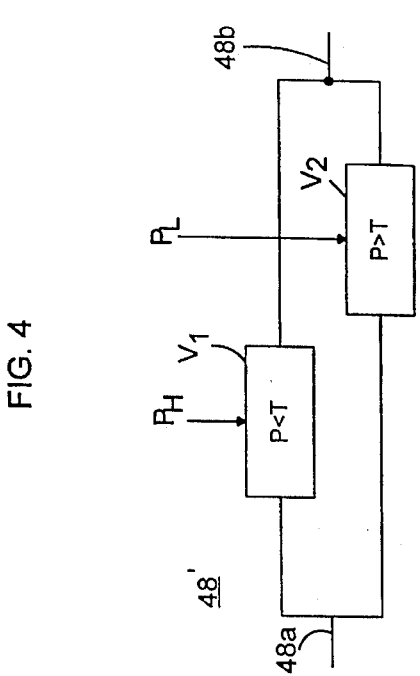
FIG. 3B shows another feedback network for the apparatus of FIG. 3.
Figure 3A:
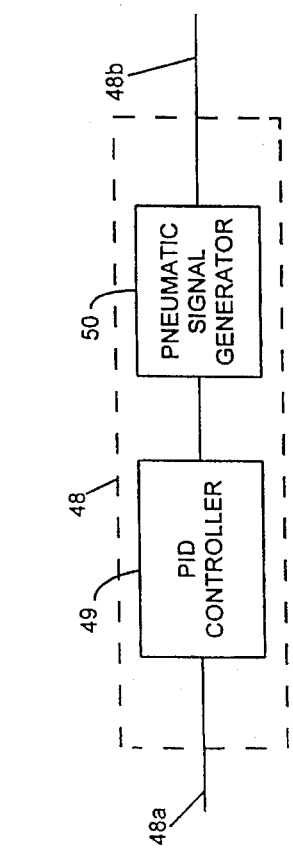
FIG. 3A shows an embodiment of the feedback network of the apparatus of FIG. 3.
Figure 3:
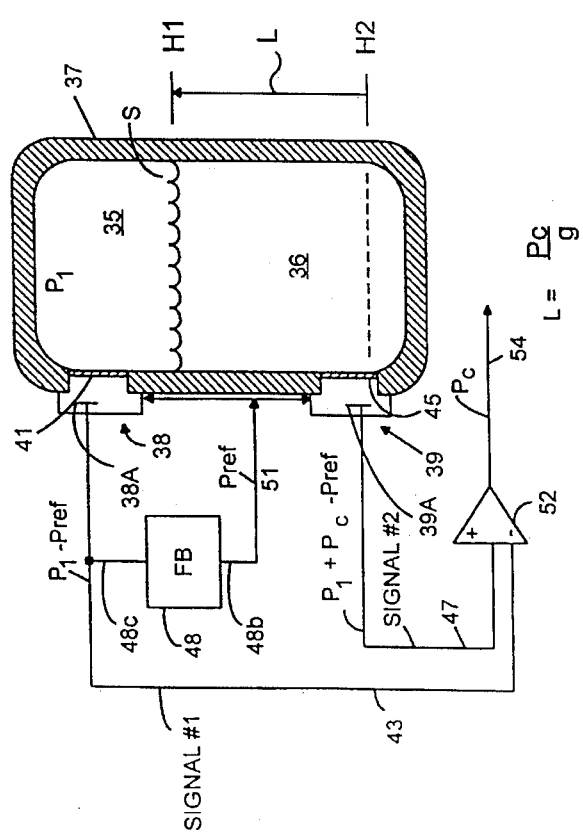
FIG. 3 shows a level measuring apparatus in accordance with one embodiment of the present invention.

FIG. 3 illustrates a level-measuring apparatus in accordance with one embodiment of the present invention for measuring the level of a liquid column 36 disposed within a sealed and pressurized cell tank 37. The interior of cell 37 includes a first region containing the liquid column 36 and a second region corresponding to an overlying blanket region 35. As used herein, the pressure of region 35, the blanket pressure, is denoted by $P_1$; the pressure of liquid column 36 is denoted by $P_C$; and the total pressure of cell 37, i.e., the liquid pressure as burdened by the blanket pressure, is denoted by $P_T$ (equalling $P_1$ plus $P_C$). The apparatus includes a first pressure sensor 38 for detecting the pressure of blanket region 35 and a second pressure sensor 39 for detecting the pressure of the entire cell 37, as described hereinafter in fuller detail.

Pressure sensor 38 is constructed from a differential diaphragm pressure sensor including a diaphragm 41 having one side in direct, pressure-sensing relationship with the interior of cell 37 near the top of cell 37, and having another side coupled to a reference pressure (via pneumatic line 51). In this embodiment, the direct connection refers to a direct coupling of the diaphragm to the interior of the cell without any intermediate linkages such as capillary tubing, and generally forms a continuation of the interior surface of cell 37. At least a portion of the diaphragm 41 is adapted to move, or deflect, transverse to its principal surface in response to a pressure differential across the diaphragm.

A conventional capacitive-type diaphragm displacement detection circuit (indicated by conductive plate 38A) provides a signal on line 43 that is representative of the position of diaphragm 41. By way of example, the diaphragm 41 is electrically conductive, and the circuit 38A may be a conventional capacitive-type circuit of the type disclosed in U.S. Pat. No. 4,054,833, in which the capacitance between the diaphragm 41 and a fixed reference plate 38A is determined and a corresponding signal is generated.

Pressure sensor 38 is affixed to cell 37 such that diaphragm 41 is above the maximum possible level of liquid column 36, enabling the diaphragm 41 to be subjected to the blanket pressure of region 35 for every possible liquid column height. The pressure detected by diaphragm 41 is measured with respect to a reference pressure $P_{ref}$ at a reference pressure port, producing a differential pressure measurement at the output 43 of sensor 38. In the illustrated embodiment, the differential pressure measurement is expressed electronically as an equivalent electrical signal.

Pressure sensor 39 is likewise a differential pressure sensor including a diaphragm 45 having one side in direct, pressure-sensing relationship with the interior of cell 37. Sensor 39 is affixed to cell 37 so that diaphragm 45 is subjected to the total pressure (i.e., liquid column pressure plus blanket pressure) in cell 37. Accordingly, sensor 39 is mounted on cell 37 so that diaphragm 45 is located at or near the bottom of cell 37. The pressure detected by diaphragm 45 is measured with respect to the reference pressure $P_{ref}$, producing a differential pressure measurement at the output 47 of sensor 39. In particular, the output from sensor 39 represents the approximate differential measurement between the total cell pressure exposed to diaphragm 45 and the pressure value $P_{ref}$ at the reference pressure port. The differential measurement appears at the output of sensor 39 as a representative electrical signal.

The particular arrangement of sensors 38 and 39 shown in FIG. 3 should not be construed as a limitation of the present invention as it should be apparent to those skilled in the art that other possible sensor arrangements may be used consistent with the present invention, provided that the operational constraints noted above are still observed. For example, the transducer for sensor 39 may be attached elsewhere to cell 37 provided that its diaphragm interacts sufficiently with liquid column 36 when coupled direct to cell 37 so as to permit detection of the entire pressure within cell 37.

As noted above, an object of the present invention is to construct a level-measuring apparatus characterized by a lower dynamic range for each pressure sensor as compared to the range required by conventional configurations. This objective is achieved as the fluid level changes by operating sensor 38 in a feedback loop, using feedback network (FB) 48, and by operating sensor 39 in an open loop. In particular, the reference pressure $P_{ref}$ is continuously adjusted so that sensor 38 is operated in a pressure balance feedback loop with the diaphragm 41 being maintained at a zero or null position. Sensor 39 operates in an open loop, providing a pressure value at output line 47 corresponding to the approximate difference between the total cell pressure and the blanket pressure.

Thus, the above principles of operation are realized using a closed-loop feedback network 48 coupled to the sensors that is responsive to changes in fluid level (as communicated through sensor 38 as a differential pressure measurement) for dynamically varying the pressure $P_{ref}$ applied to the reference ports of both sensors such that the required dynamic range for measuring the accompanying pressure change is small. The feedback network is operative to cause the reference pressure of sensor 38 to maintain the diaphragm at a null position, establishing a nearly zero differential pressure measurement at output 43. In difference network 52, the signal on line 43 is differenced with the signal on line 47 to produce on line 54 measurement value $P_C$ corresponding to the pressure of the liquid column between the position of sensor 39 and the surface level S of the liquid column.

The importance of this feedback network may be demonstrated with a comparison to conventional gauge-type sensor devices. For gauge-type configurations, each sensor measures the pressure for its region of interest (e.g., blanket region or total cell) with respect to a constant value such as atmospheric pressure. However, as the fluid level changes in the present invention, sensor 38 detects pressure variations relative to its zero or null differential pressure condition, while sensor 39 detects pressure variations relative to its open-loop condition (i.e., total cell pressure less blanket pressure).

FIG. 3A shows an exemplary feedback network 48 having input line 48a (coupled to line 43) and output line 48b (coupled to line 51). Network 48 translates the differential pressure measurement from sensor 38 into an equivalent pneumatic signal that is supplied as the reference pressure $P_{ref}$ to each of the reference pressure ports of sensors 38 and 39. The feedback network 48 is responsive to pressure changes in the blanket region (arising from changes in the fluid level) for driving the reference pressure of both sensors to the blanket pressure that exists in region 35. In particular, as the fluid level changes in cell 37, pressure changes in region 35 are communicated through the diaphragm 41 as pressure variations. The differential measurement at sensor output 43 is indicative of these pressure variations, which are then transformed to a corresponding pneumatic signal. The pneumatic signal serves as a feedback signal that is used to ensure that the reference pressure of sensor 38 automatically tracks the pressure of the blanket region as the fluid level changes.

In a preferred implementation shown in FIG. 3A, feedback network 48 includes a proportional-plus-integral-plus-derivative (PID) controller 49 and pneumatic signal generator 50. The PID controller 49 is responsive to a sensor signal (Signal #1) produced by sensor 38 on line 43, and representative of the differential pressure measurement of sensor 38, for generating a compensation signal in accordance with a compensator transfer function. The compensation signal is indicative of any deviation of the sensor signal from its value at zero differential pressure that would occur from a change in fluid level. Specifically, the compensation signal C is related to the differential measurement D in accordance with:

$$C=(k_1+k_2/s+k_3s)D,$$

wherein $k_1$, $k_2$, and $k_3$ are constants and $s=jw$ where w is frequency.

With the configuration in FIG. 3A, the pneumatic signal generator 50 is responsive to the compensation signal from PID controller 49 for generating a pneumatic signal on line 51. The pneumatic signal is applied to the reference pressure ports of both sensor 38 and 39, and therefore becomes the reference pressure $P_{ref}$ used by the sensors in calculating the differential pressure measurements. This pneumatic signal is substantially equal to a pressure sufficient to cause diaphragm 41 to remain at or near its null position so that the "error" signal on line 43 is substantially nulled. The pneumatic signal generator 50 is preferably constructed from an arrangement of electromechanical valves coupled to a pressure source. With the configuration of FIG. 3B, network 48' when used with the system of FIG. 3, forms a pressure balance loop, substantially nulling the position of diaphragm 41.

Other types of feedback networks may be used; for example, FIG. 3B shows another network 48' which includes a high pressure source $P_H$, a low pressure source $P_L$ and two valves $V_1$ and $V_2$ coupled in parallel between input line 48a and output line 48b. Each of the valves has an associated threshold T which is between the pressure of sources $P_H$ and $P_L$. When the pressure on line 48a is below a threshold T, valve $V_1$ opens and the pressure source $P_H$ is coupled to line 48b; otherwise valve $V_1$ is closed. Similarly, when the pressure on line 48a is greater than threshold T, valve $V_2$ opens and the pressure source $P_L$ is coupled to line 48b; otherwise valve $V_2$ is closed. Other feedback networks responsive to the pressure of blanket region 35 may also be used.

In real time, the ability of the feedback network to drive sensor 38 into fully-balanced equilibrium (i.e., true zero differential pressure for sensor 38) is limited only by the rate at which the pneumatic valves are able to generate the pneumatic signal for $P_{ref}$. Thus, the pressure sensor outputs will experience an uncertainty consisting of the difference between the pneumatic signal and the true blanket pressure applied to sensor 38. However, since the actual liquid level pressure is computed as the difference between Signal #2 (at output of sensor 39 on line 47) and Signal #1 (at output of sensor 38 on line 43), the absolute accuracy of the pneumatic signal conversion is not a critical parameter. That difference is generated by difference amplifier 52, which provides an output signal representative of the liquid level on line 54. The utilization of two differential pressure sensors in the feedback configuration permits the cancellation of any inaccuracy resulting from the signal to pneumatic conversion, whereas in the aforementioned conventional apparatus employing two differential sensors the conversion inaccuracy is not cancellable but is additive to the total system inaccuracy.

For illustrative purposes, it is initially assumed that the fluid level within liquid column 36 is stabilized at a certain height. Hence, by operation of feedback network 48, which drives $P_{ref}$ to the existing pressure of the blanket region, sensor 38 may be considered to be in its initial steady-state condition (i.e., zero differential pressure at output 43) and sensor 39 may be considered to be in its initial steady-state condition (i.e., differential pressure at output 47 equalling total cell pressure less blanket pressure, resulting in liquid column pressure). If the fluid level is decreased by drawing fluid from tank 37, the pressure of the blanket region will decrease due to an increased volume, while the pressure of the liquid column will decrease in a manner related to the amount of liquid drawn from tank 37. This decrease in blanket pressure will nominally cause the differential measurement of sensor 38 to change by a deviation value $\epsilon_1$ from its null or zero differential pressure condition to some non-zero differential measurement value. Additionally, the decrease in column liquid pressure will cause the differential measurement of sensor 39 to change by a deviation value $\epsilon_2$ from its steady-state column pressure value.

By operation of feedback network 48, the deviation value $\epsilon_1$ is translated into an equivalent pneumatic signal, which when applied to the reference port of sensor 38 will drive the diaphragm 41 back to its zero differential pressure condition whereby the reference pressure is equalized to the blanket pressure presently being detected by diaphragm 41. As shown in FIG. 3, the pneumatic signal from feedback network 48 is also coupled to the reference pressure port of sensor 39. Since the pressure detected by diaphragm 45 represents the composite pressure from blanket region 35 and liquid column 36, and the reference pressure of sensor 39 is driven by feedback network 48 to track the blanket pressure, the differential measurement at output 47 is the existing pressure of the liquid column. By selecting a suitable feedback time constant (i.e., the response rate of the loop in comparison to the rate at which changes in liquid level may occur), the pressure balance loop may maintain diaphragm 41 substantially at its null position.

The present invention features a dynamic range for pressure sensors 38 and 39 that is significantly lower than the range required by some prior art apparatus. In certain conventional configurations such as gauge-type apparatus, each pressure transducer obtains measurements in relation to a constant reference pressure value, typically atmospheric pressure. For the upper transducer measuring the blanket pressure, this means that the dynamic range in such conventional configurations must extend to the maximum possible blanket pressure value. In contrast, the present invention is operative so that the dynamic range of sensor 38 is defined only by the nominal variation $\epsilon_1$ of output 43 from zero differential pressure as the pressure of the blanket region changes in response to changes in fluid level. Moreover, with respect to the lower transducer measuring total cell pressure in conventional gauge-type devices, the dynamic range must extend over the range of the total cell pressure. However, in the present invention, the dynamic range of sensor 39 is only required to track the range of pressure attributable to pressure variations of the liquid column. Accordingly, in the present invention, the differential measurement for sensor 39 is advantageously optimized to the liquid level being measured (i.e., total cell pressure detected by sensor 39 less the current blanket pressure supplied by feedback system 48), whereas gauge-type devices require a full scale range for the lower transducer at least as high as the total pressure.

In applications requiring the level height of liquid column 36, this height value may be determined from the true pressure of the liquid column as computed above.

Figure 4:
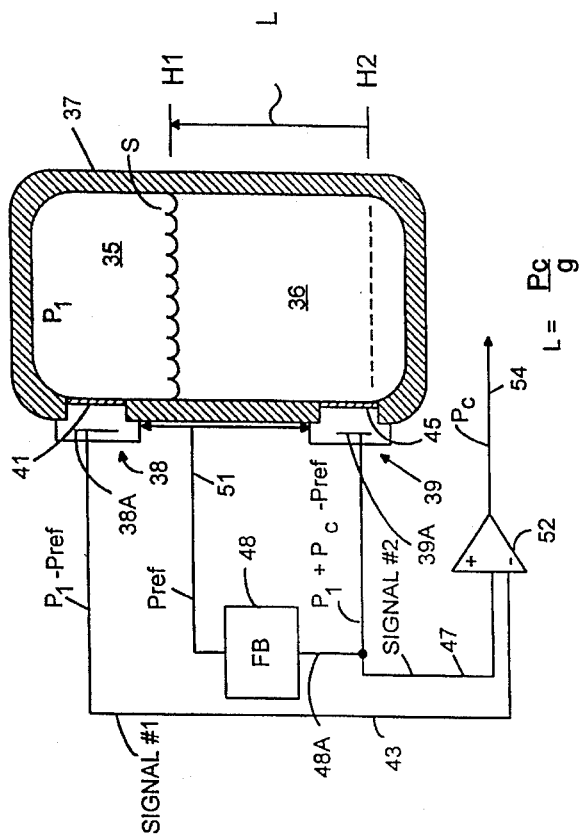
FIG. 4 shows another embodiment of the level measuring apparatus in accordance with the invention.

In accordance with another embodiment of the present invention, shown in FIG. 4, the feedback network 48 may be positioned between lines 47 and 51, so that the diaphragm 45 of transducer 39 is nulled while the diaphragm 41 of transducer 38 is open loop. Otherwise, the configuration of FIG. 4 is similar to that of FIG. 3.

Figure 5:
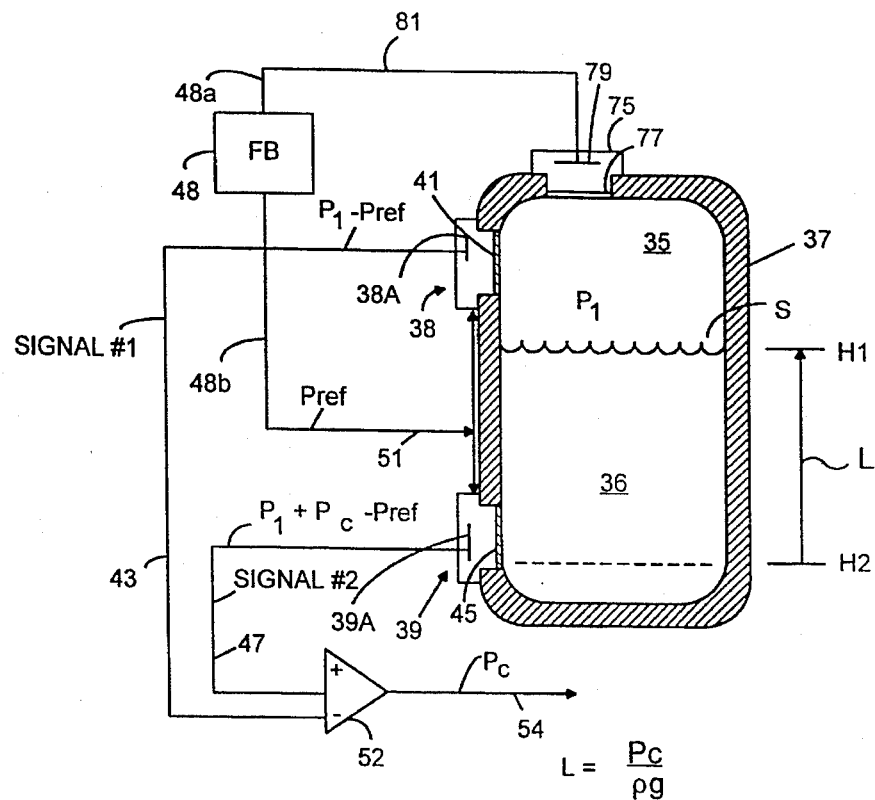
FIG. 5 shows yet another embodiment of the level measuring apparatus in accordance with the invention.

FIG. 5 shows another level-measuring apparatus, configured similarly to the apparatus of FIG. 3, but incorporating a third differential sensor 75 that is disposed on the top wall of cell 37. Sensor 75 includes a diaphragm 77 and sensing circuit 79 that provides a signal on line 81 representative of the blanket pressure $P_1$. The signal on line 81 is applied to feedback network 48 which in turn generates the reference pressure $P_{ref}$ applied via line 51 to the reference input of sensors 38 and 39. Generally, the configuration of FIG. 5 operates in the same manner as that of FIG. 3.

The level measuring configuration of the present invention offers several advantages over conventional systems. For example, the present invention employs differential pressure sensors coupled to the cell with a direct coupled diaphragm, avoiding the use of liquid-filled capillary tubing employed in conventional systems. Additionally, the dynamic range required for the sensor that measures the entire cell pressure is reduced since the widely varying blanket pressure is applied to the reference port of both sensors, so that the sensor only has to respond to relatively small pressure changes caused by the liquid column. The reduction in required dynamic range permits use of lower cost sensors for a given measuring capability.

Figure 6:
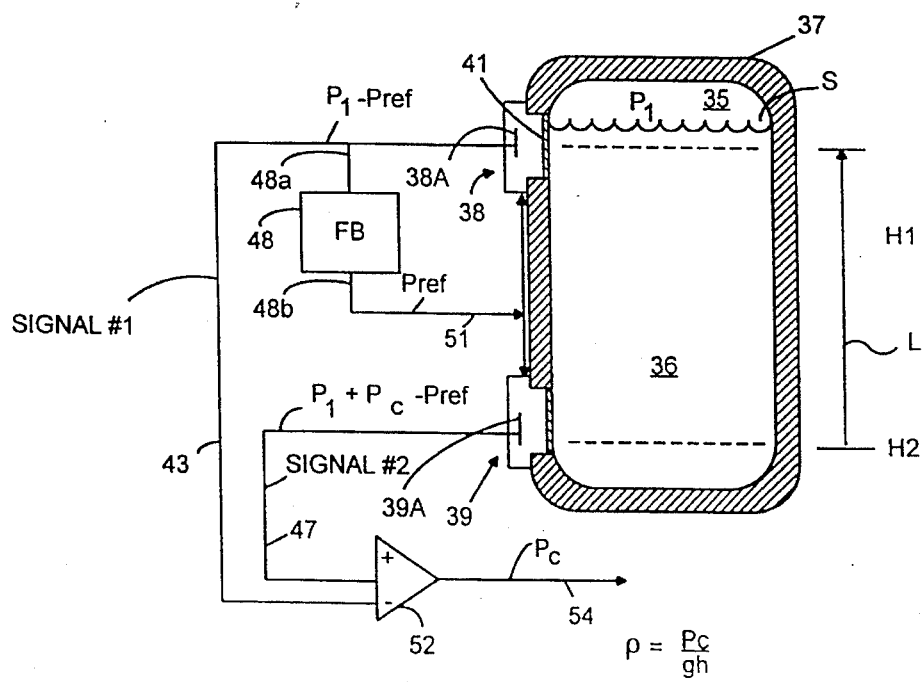
FIG. 6 shows a density measuring apparatus in accordance with the invention.

FIG. 6 shows a system similar to that of FIG. 3, but where both sensors 38 and 39 are below the surface level S of the liquid in cell 37. With that configuration, the signal $P_c$ in line 54 may be used to determine the density $\rho$ of the liquid in accordance with $\rho = P_c/gh$.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes that come within the meaning and range of equivalency of the claims are therefore intended to be embraced therein.

What is claimed is:

1. An apparatus for measuring a characteristic of a liquid column in a cell having a blanket region overlying said liquid column said blanket region being characterized by a blanket pressure $P_1$, comprising:

A. first pressure sensing means for differentially generating a first signal representative of the pressure of said cell at a first height H1 with respect to a reference pressure;

B. second pressure sensing means for differentially generating a second signal representative of the pressure of said cell at a second height H2 with respect to said reference pressure, said second height being lower than said first height, and C. feedback means for substantially equalizing said reference pressure with the pressure of said cell at one of said first and second heights.

2. An apparatus according to claim 1 further comprising means for generating an output signal $P_c$ representative of the difference of said first signal and said second signal.

3. The apparatus according to claim 2 wherein the H1 and H2 are below the level of said column, and wherein said apparatus further includes means for determining the density $\rho$ of said liquid in accordance with:

$$\rho = P_c/gh$$

where g is the gravitational constant and h=H1−H2.

4. The apparatus according to claim 2 wherein H1 is above the level of said column and H2 is below the level of said column, and wherein said apparatus further includes means for determining said level L measured with respect to H2, in accordance with $$L = P_c/g\rho$$

where g is the gravitation constant and $\rho$ is the density of said liquid.

5. An apparatus according to claim 1 wherein said first and second sensing means each include a reference port coupled to said reference pressure, and wherein said feedback means is coupled between said first pressure sensing means and said reference ports of said first and second pressure sensing means.

6. An apparatus according to claim 1 wherein said first and second sensing means each include a reference port coupled to said reference pressure, and wherein said feedback means is coupled between said second pressure sensing means and said reference ports of said first and second pressure sensing means.

7. An apparatus according to claim 1 wherein said feedback means further includes a third pressure sensing means positioned at or near the top of said cell, and wherein said first and second sensing means each include a reference port coupled to said reference pressure, and wherein said feedback means is coupled between said third pressure sensing means and said reference ports of said first and second pressure sensing means.

8. The apparatus as recited in claims 1 or 5 or 6 or 7, wherein each of said first and second pressure sensing means comprises:

A. a differential pressure sensor having a diaphragm coupled on one side to a region interior to said cell, and on another side to a region distinct from said interior region, and having a reference port in pneumatic communication with said reference pressure, wherein at least a portion of said diaphragm is moveable in response to pressure differentials applied across said diaphragm; and B. position sensing means for generating a signal representative of the position of said portion of said diaphragm.

9. The apparatus as recited in claim 8 wherein said feedback means comprises:

a proportional-plus-integral-plus-derivative controller responsive to the differential measurement from said first pressure sensing means, including means for generating a compensation signal, said compensation signal C being related to said differential measurement D in accordance with:

$$C=(k_1+k_2/s+k_3 s)D,$$

wherein $k_1$, $k_2$, and $k_3$ are constants and $s=jw$ where w is frequency;

pneumatic signal means responsive to the compensation signal for generating a pneumatic signal that is representative of said compensation signal; and means for applying the pneumatic signal as the reference pressure to each of said first and second pressure sensing means.

10. An apparatus for determining the level of a liquid column in a sealed, pressurized cell having a blanket region overlying said liquid column, comprising:

first pressure sensor means positioned above the surface level of said liquid column in pressure-sensing relationship with said blanket region for generating a first sensor signal representative of the pressure difference between the pressure in said blanket region and a reference pressure;

second pressure sensor means positioned below the surface level of said liquid column in pressure-sensing relationship with said liquid column at or near the bottom of said column for generating a second sensor signal representative of the pressure difference between pressure caused by said column as burdened by the pressure in said blanket region and said reference pressure; and feedback means responsive to said first sensor signal for continuously adjusting said reference pressure to substantially match the pressure of said blanket region.

11. The apparatus according to claim 10 further comprising means for generating an output signal representative of the difference between said first and second sensor signals, said output signal being representative of said level.

12. The apparatus as recited in claim 11 wherein each of said first and second pressure sensor means comprises:

A. a differential pressure sensor having a diaphragm coupled on one side to a region interior to said cell, and on another side to a region distinct from said interior region, and having a reference port in pneumatic communication with said reference pressure, wherein at least a portion of said diaphragm is moveable in response to pressure differentials applied across said diaphragm; and B. means for generating a signal representative of the position of said portion of said diaphragm.

13. The apparatus as recited in claim 12 wherein said feedback means comprises:

a proportional-plus-integral-plus-derivative controller responsive to the differential measurement from said first pressure sensing means, including means for generating a compensation signal, said compensation signal C being related to said differential measurement D in accordance with:

$$C=(k_1+k_2/s+k_3 s)D,$$

wherein $k_1$, $k_2$, and $k_3$ are constants and $s=jw$ where w is frequency;

pneumatic signal means responsive to the compensation signal for generating a pneumatic signal that is representative of said compensation signal; and means for applying said pneumatic signal as the reference pressure to each of said first and second pressure sensor means.

14. A method of determining the level of a liquid column contained within a pressurized cell and having a blanket region overlying said liquid column, comprising the steps of:

generating a blanket pressure signal representative of the pressure difference between the pressure in said blanket region and a reference pressure at a first height H1, where H1 is above the level of such liquid column;

generating a cell pressure signal representative of the pressure difference between pressure caused by said column as burdened by the pressure in said blanket region and said reference pressure at a second height H2, where H2 is lower than H1, and H2 is below the level of said liquid column;

generating a pneumatic signal representative of said blanket pressure signal; and dynamically adjusting said reference pressure in accordance with said pneumatic signal whereby the difference between said blanket pressure signal and said cell pressure signal is representative of said level measured with respect to H2.

15. The method as recited in claim 14 including the substep of selecting H2 to be at or near the bottom of said cell.

16. The method as recited in claim 14 wherein said step of dynamically adjusting said reference pressure comprises the steps of:

generating a compensation signal in response to the blanket pressure signal, said compensation signal C being related to said differential measurement D in accordance with:

$$C=(k_1+k_2/s+k_3 s)D,$$

wherein $k_1$, $k_2$, and $k_3$ are constants and $s=jw$ where w is frequency;

generating said pneumatic signal whereby said pneumatic signal is representative of said compensation signal; and utilizing said pneumatic signal as said reference pressure.

* * * * *